United States Patent

Askham

[11] Patent Number: 5,965,757
[45] Date of Patent: Oct. 12, 1999

[54] SYNTHESIS OF N-SILYLATED CYCLOPENTAPHENANTHRENE COMPOUNDS

[75] Inventor: Fredric Askham, Loveland, Colo.

[73] Assignee: Boulder Scientific Company, Mead, Colo.

[21] Appl. No.: 09/018,534

[22] Filed: Feb. 4, 1998

[51] Int. Cl.$^6$ ................... C07F 17/00; C07F 7/00
[52] U.S. Cl. ................... 556/11; 556/12; 556/53; 556/410; 556/466; 502/103; 502/117; 526/160; 526/943; 585/441
[58] Field of Search .................. 556/11, 12, 53, 556/410, 466; 502/103, 117; 526/160, 943; 585/441

[56] References Cited

PUBLICATIONS

Schneider et al., Organometallics, vol. 16, pp. 3413–3420, 1997.

*Primary Examiner*—Porfirio Nazario-Gonzalez
*Attorney, Agent, or Firm*—Edward S. Irons

[57] ABSTRACT

A method for the synthesis of certain N-silylated cyclopentaphenanthrene (Group IV metal) complexes is disclosed.

8 Claims, No Drawings

SYNTHESIS OF N-SILYLATED CYCLOPENTAPHENANTHRENE COMPOUNDS

This application is related to Gately application Ser. No. 09/016,641 filed Jan. 30, 1998 and entitled "Silylated and N-Silylated Compound Synthesis".

FIELD OF INVENTION

This invention relates to the synthesis of N-silylated cyclopentaphenanthrene (Group IV metal) complexes.

BACKGROUND OF THE INVENTION

It is known to react lithium salts of N-silylated metallocene ligands with a Group IV metal halide wherein a metallocene compound useful as an olefin polymerization catalyst may be produced.

SUMMARY OF THE INVENTION

This invention provides methodology useful to produce ligands from which N-silylated cyclopentaphenanthrene (Group IV metal) complexes useful as olefin polymerization catalysts may be synthesized.

An example of the methodology of the invention may include:

(1) conversion of phenanthrene to 2,3 dehydro-1-oxycyclopentaphenanthrene (Compound A):

COMPOUND A

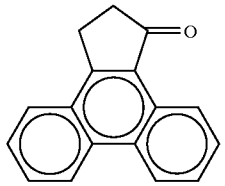

(2) conversion of 2,3 dehydro-1-oxycyclopentaphenanthrene to 1H cyclopentaphenanthrene (Compound B):

COMPOUND B

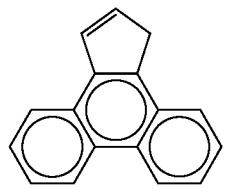

(3) conversion of 1H cyclopentaphenanthrene to produce Compound C:

COMPOUND C $(CH_3)_2SiNHR$

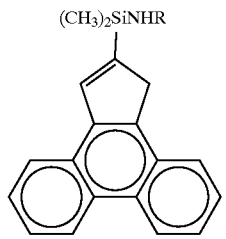

in which R is an alkyl group, preferably a t-butyl group; and (4) conversion of Compound C to Compound D:

COMPOUND D $(CH_3)_2$—Si——NR
         |
         $MCl_2$

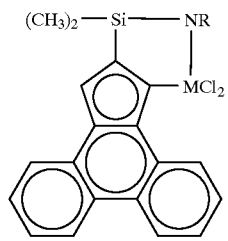

in which R is an alkyl group, preferably a t-butyl group, and M is a Group IV metal, e.g., zirconium, titanium or hafnium.

Preferably this conversion is accomplished by reacting Compound C with a Group IV metal secondary amide complex and an excess of $(CH_3)_3$ SiCl or its equivalent.

DETAILED DESCRIPTION OF THE INVENTION

The steps or subcombination of steps which may comprise each aspect of the invention are sequentially described.

Production of Compound A:

Methods are known for the synthesis of Compound A. See, e.g., Schneider, et al., *Organometallica* (1997) 16:3414–3420, specifically page 3416, Scheme 1 and Scheme 2 and the product 12 produced in Scheme 2.

Production of $^1$H Cyclopentaphenanthrene Compound B:

Scheme 2 of Schneider, et al., also describes the conversion of Compound A to Compound B.

This invention provides a different method for that conversion which includes (i) reacting Compound A at a temperature of −50° C. to 120° C., preferably, but not necessarily, in a proportion of about 2 to 3 mols of hydrazide per mol of Compound A with tosyl hydrazide in a medium comprising an aromatic hydrocarbon solvent, preferably toluene, and 1 to 20 mol percent, preferably 10 mol percent of a one to five carbon atom fatty acid, preferable acetic acid wherein the corresponding tosyl hydrazone is produced. Benzene, xylene, or mesitylene may be used instead of toluene. See Equation 1 and Example I. Functionally equivalent hydrazide other than tosyl hydrazide, e.g., phenylhydrazide are known to those skilled in the art and may be used in this method.

EQUATION 1

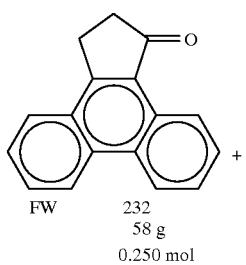

FW 232
58 g
0.250 mol

+

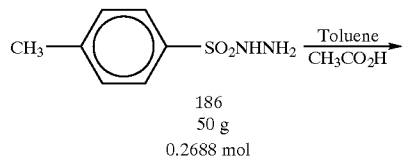

186
50 g
0.2688 mol

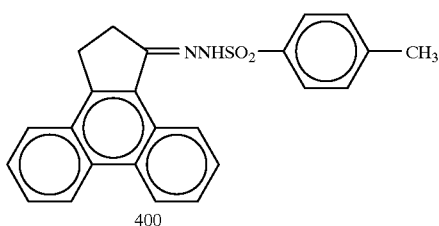

400

EXAMPLE I

As indicated by Equation 1, 0.250 mol of Compound A and 0.686 mol of tosylhydrazide are combined in a mixture containing 1 l. toluene and 13 ml acetic acid. This reaction mixture is heated and a small portion, i.e., less than 50%, of the reaction solvent is distilled over five hours. The residual reaction mixture is then cooled to room temperature and filtered. The filter cake was washed with 100 ml toluene followed by 100 ml hexanes and vacuum dried the product. Yield=90 g (90% $^1$H NMR).

The hydrazone product of Equation 1 is converted to $^1$H cyclopentaphenanthrene (Compound B) as indicated by Equation 2:

EQUATION 2

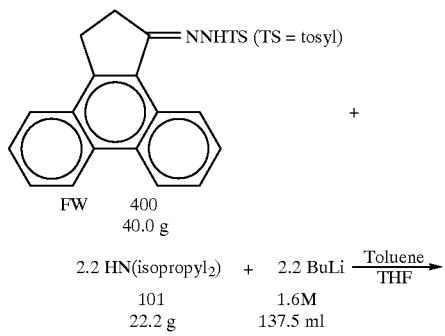

FW 400
40.0 g

+

2.2 HN(isopropyl$_2$) + 2.2 BuLi $\xrightarrow{\text{Toluene}}$
                                         THF
101            1.6M
22.2 g         137.5 ml -continued

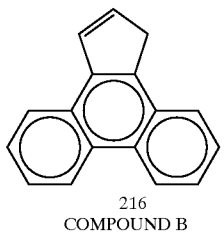

216
COMPOUND B

EXAMPLE II 22.2 g of diisopropylamine was diluted with 200 ml THF under N$_2$ and cooled in an ice/water bath. 1.6M BuLi was added over 20 minutes. The mixture was stirred one-half hour after completion of the BuLi addition. The lithium diisopropylamide (LDA) solution thus formed was added over five minutes to a suspension of 40 grams of the tosylhydrazone in 500 ml toluene. This mixture was stirred overnight. 10 ml H$_2$O was then added and the resulting mixture was then stirred thirty minutes. 120 g celite was added. This mixture was stirred for ten minutes and then filtered. The filtrate was concentrated under vacuum to give 18.6 g of a light brown solid (86%) dehydrocyclopentaphenanthrene (Compound B).

Other aromatic hydrocarbon solvents, e.g., benzene, xylene, mesitylene may be used instead of toluene. Any secondary amine having one to five carbon atom alkyl groups may be used instead of diisopropyl amine. Appropriate proportions of reactants are 1 mol of hydrazone per 2 to 3 mols of secondary amine and 2 to 3 mols of butyl lithium.

One series of steps useful to convert $^1$H cyclopentaphenanthrene (Compound B) to Compound C is illustrated by Equations 3, 3(a) and Example 3:

EQUATION 3

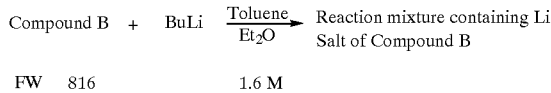

FW    816              1.6 M
      32.1 g           92.9 ml
      0.1486 mol       0.1486

EQUATION 3(a)

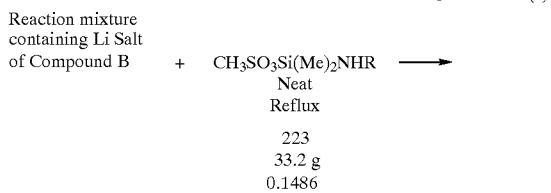

in which R is as defined, preferably t-butyl.

EXAMPLE III

As illustrated by Example III, $^1$H cyclopentaphenanthrene (Compound B) was combined with and mostly dissolved in 700 ml toluene; 16 ml diethyl ether was added followed by N-butyl lithium; precipitation of the lithium salt of Compound B occurred within 15 minutes.

The reaction mixture was stirred overnight at room temperature. In this reaction, ethyl ether, $Et_2O$ may be replaced by any ether having the formula $R^1OR^2$ wherein $R^1$ and $R^2$ are identical or different one to five carbon atom alkyl groups. The ether is preferably used in an amount corresponding to 2 moles of ether per 1 to 2 moles of Compound B.

As illustrated by Equation 3(a), $CH_3SO_3Si(CH_3)_2NH$ (t-butyl) was added neat to the Equation 3 reaction mixture. This mixture was refluxed overnight, cooled to room temperature and filtered. Toluene was removed under vacuum.

Yield—50 g brown solid which was >90% pure Compound C. ($^1H$ NMR).

Equimole proportions of Compound B and $CH_3SO_3Si(Me)_2NHR$, wherein R is preferably t-butyl, are appropriate.

As illustrated by Example III, the conversion of Compound B to Compound C may be accomplished in a single pot. Alternatively, the lithium salt may be separated and then converted to Compound C.

One series of steps useful to convert Compound C to pound D is illustrated by Equation 4:

EQUATION 4

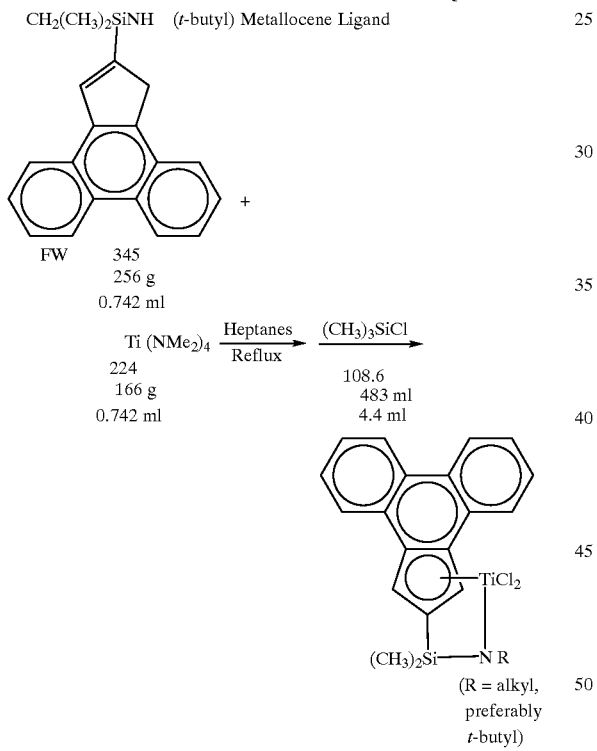

EXAMPLE IV 256 g of Compound C was added to 5 liters of heptanes in which it mostly dissolved at 50° C. The solution was filtered to remove a small amount of insoluble material. The filtrate was heated to reflux under nitrogen. 158 ml of $Ti(NMe_2)_4$ was then added by syringe. The reaction mixture was refluxed for three hours, then cooled to room temperature. Chlorotrimethylsilane (400 g) was added and refluxed four hours, cooled to room temperature and filtered. Filter cake was washed with 2×500 ml toluene, followed by 500 ml hexanes and dried under vacuum. 257 g (75% yield) of Yellow solid was obtained.

I claim:
1. A method which comprises:
   (i) reacting 2,3-dihydro-1-oxocyclopentaphenanthrene (Compound A) with tosylhydrazide wherein a first reaction mixture containing the tosylhydrazone compound:

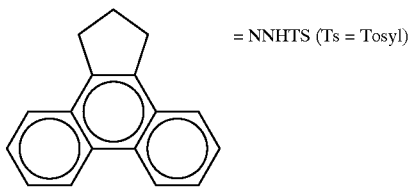

is produced
   (ii) reacting said tosylhydrazone compound produced in step (i) with a secondary amine and a butyl lithium in a mixed toluene and tetrahydrofuran medium wherein a second reaction mixture containing 1-H cyclopentaphenanthrene (Compound B) is produced.

2. The claim 1 method further comprising step (iii) converting said 1-H cyclopentaphenanthrene Compound B produced in step (ii) to Compound C having the formula:

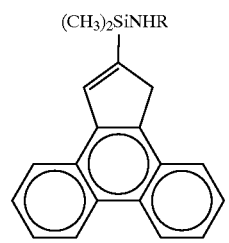

wherein R is an alkyl group.

3. The claim 2 method wherein R is t-butyl.

4. A method which comprises:
   (i) reacting 2,3-dehydro-1-oxycyclopentaphenanthrene with tosylhydrazide having the formula

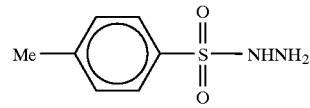

in a non-interfering solvent wherein a tosylhydrazone compound having the formula:

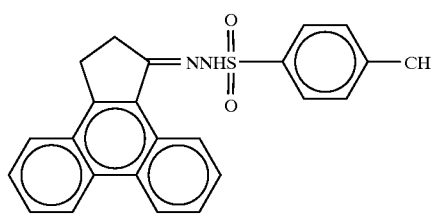

is produced;
   (ii) reacting the tosylhydrazone produced in step (i) with $LiN(R)_2$ wherein R is a one to six carbon atom alkyl group, in a non-interfering medium to produce $^1H$ cyclopentaphenanthrene having the formula:

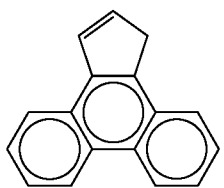

(iii) reacting the ¹H cyclopentaphenanthrene product of step (ii) with butyl lithium and CH₃SO₃Si(CH₃)₂(t-butyl) wherein an N-silylated compound having the formula:

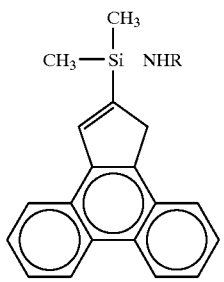

wherein R is n alkyl group is produced;

(iv) reacting said n-silylated compound produced in step (iii) with Ti(NMe₂)₄ and (Me)₃SiCl wherein a titanocene compound having the formula:

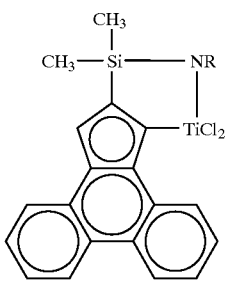

is produced.

5. The claim 4 method wherein R is t-butyl.

6. A method which comprises (i) reacting cyclopentaphenanthrene with butyl lithium in a mixed toluene and ether solvent
wherein a first reaction mixture containing lithiated cyclopentaphenanthrene in said solvent mixture is produced; and (ii) reacting CH₃SO₃Si(CH₃)₂NHR with said lithiated cyclopentaphenanthrene contained in step (i) first reaction mixture
wherein a second reaction mixture is produced and
wherein said second reaction mixture contains the compound

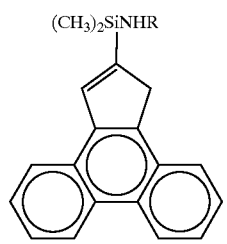

wherein R is an alkyl group.

7. The claim 6 method in which R is t-butyl.

8. The claim 6 method further comprising separating said compound

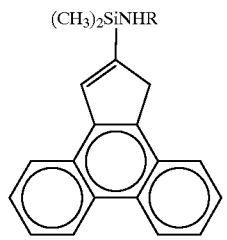

from said second reaction mixture.

* * * * *